(12) United States Patent
Yoo

(10) Patent No.: US 9,743,695 B2
(45) Date of Patent: Aug. 29, 2017

(54) WEARABLE DEVICE

(71) Applicant: Samsung Electronics Co., Ltd., Gyeonggi-do (KR)

(72) Inventor: Jung-Heon Yoo, Yongin-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 111 days.

(21) Appl. No.: 14/697,091

(22) Filed: Apr. 27, 2015

(65) Prior Publication Data

US 2015/0320128 A1 Nov. 12, 2015

(30) Foreign Application Priority Data

May 7, 2014 (KR) .................. 10-2014-0054419

(51) Int. Cl.
| | | |
|---|---|---|
| *A41D 20/00* | (2006.01) | |
| *A44C 5/14* | (2006.01) | |
| *G04G 17/00* | (2013.01) | |
| *G06F 1/00* | (2006.01) | |
| *G04G 21/04* | (2013.01) | |
| *G04B 37/14* | (2006.01) | |

(52) U.S. Cl.
CPC ............. *A41D 20/00* (2013.01); *A44C 5/14* (2013.01); *G04B 37/1486* (2013.01); *G04G 17/00* (2013.01); *G04G 21/04* (2013.01); *G06F 1/00* (2013.01)

(58) Field of Classification Search
CPC .... A41D 20/00; A41D 13/08; G04B 37/1486; G04B 37/0025

USPC ...... 2/170, 16, 162, 910; 368/281, 282, 283; 224/173
See application file for complete search history.

(56) References Cited

U.S. PATENT DOCUMENTS

| | | | | |
|---|---|---|---|---|
| 3,307,345 A | * | 3/1967 | Cohen ............... | G04B 37/14 224/152 |
| 5,838,642 A | * | 11/1998 | Tully ................. | A41D 20/00 224/171 |
| 7,210,844 B2 | * | 5/2007 | Hiranuma .......... | G04B 37/1486 224/177 |
| 2012/0168471 A1 | * | 7/2012 | Wilson .............. | A45F 5/00 224/152 |
| 2014/0049004 A1 | * | 2/2014 | Del Valle .......... | A41D 20/00 273/148 R |
| 2015/0342308 A1 | * | 12/2015 | Wilson .............. | A45F 5/00 224/219 |

FOREIGN PATENT DOCUMENTS

| | | | |
|---|---|---|---|
| KR | 10 19870011516 A | 12/1987 | |
| KR | 10 19980087678 A | 12/1998 | |

* cited by examiner

*Primary Examiner* — Tejash Patel

(57) ABSTRACT

A wearable device comprises a body portion, a strap portion coupled with the body portion, the strap portion provided to allow the body portion to be worn on a human body, and a connection module provided in a portion of the strap portion and a portion of the body to couple the strap portion with the body portion. The connection module comprises a connection pin portion provided in the strap portion to detachably couple the strap portion with the body portion and a holder portion provided in an end of the strap portion, the connection pin portion inserted in the holder portion.

19 Claims, 11 Drawing Sheets

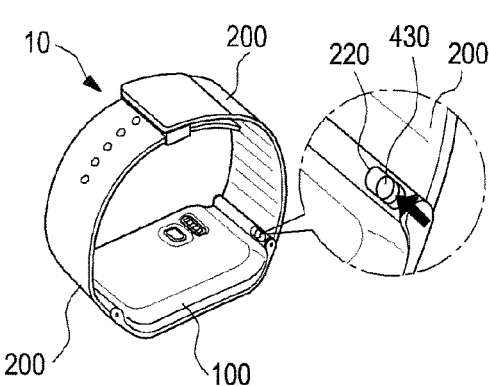
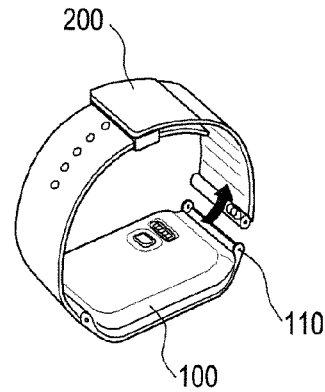
FIG.11A  FIG.11B
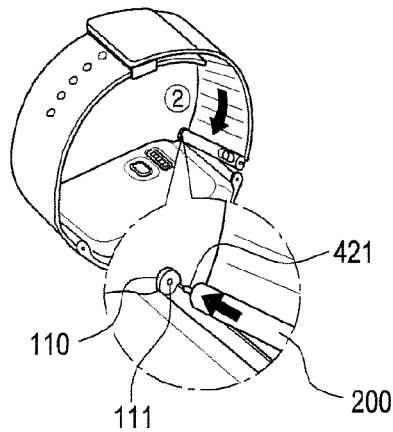
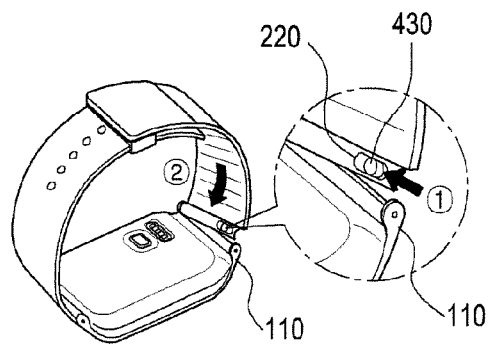
FIG.11C  FIG.11D
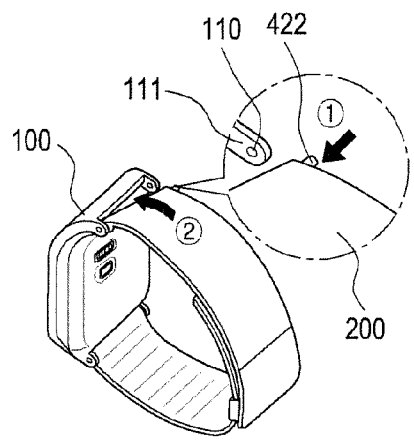
FIG.11E

WEARABLE DEVICE

CROSS-REFERENCE TO RELATED APPLICATION(S) AND CLAIM OF PRIORITY

The present application is related to and claims the benefit under 35 U.S.C. §119(a) of a Korean patent application filed in the Korean Intellectual Property Office on May 7, 2014 assigned Serial No. 10-2014-0054419, the entire disclosure of which is incorporated herein by reference.

TECHNICAL FIELD

Embodiments of the present disclosure concern wearable devices, and for example, connection modules provided for allowing a device to be put on a human body.

BACKGROUND

There are various types of wearable devices, such as wristwatches, smartwatches, or bio signal detectors, which may be worn on the user's body, particularly on his wrist. A wrist-mounted wearable device may include a device casing, a pair of straps, and connection pins for coupling the straps to the casing. A diversity of materials come into availability for the straps.

The straps, when formed of a non-metallic material, e.g., urethane, silicone, carbon, leather, or fabric, are vulnerable to tear or wear from repetitive use or frequent swapping.

Use of a tool for releasing the straps out of the casing may damage or deform the straps.

The above information is presented as background information only to assist with an understanding of the present disclosure. No determination has been made, and no assertion is made, as to whether any of the above might be applicable as prior art with regard to the present disclosure.

SUMMARY

To address the above-discussed deficiencies, it is a primary object to provide a wearable device with coupling bands prevented from damage upon repetitive removal or installation.

According to an embodiment of the present disclosure, there is provided a wearable device with coupling bands subject to easier removal/installation.

According to an embodiment of the present disclosure, there is provided a wearable device with connection pin portions prevented from fiddling upon removal or installation of coupling bands.

According to an embodiment of the present disclosure, a wearable device comprises a body portion, a strap portion coupled with the body portion, the strap portion provided to allow the body portion to be worn on a human body, and a connection module provided in a portion of the strap portion and a portion of the body to couple the strap portion with the body portion, wherein the connection module comprises a connection pin portion provided in the strap portion to detachably couple the strap portion with the body portion and a holder portion provided in an end of the strap portion, the connection pin portion inserted in the holder portion.

According to an embodiment of the present disclosure, a wearable device comprises a body portion, a strap portion coupled with the body portion, the strap portion provided to allow the body portion to be worn to a human body, and a connection module provided between the body portion and the strap portion to couple the strap portion with the body portion, wherein the connection module comprises a connection pin portion including a knob adjacent to an end thereof, the knob exposed to an outside of the strap portion, wherein the knob is driven to couple or decouple the strap portion to/from the body portion and a holder portion provided in an end of the strap portion, the connection pin portion inserted in the holder portion.

According to embodiments of the present disclosure, the wearable device includes the holder portion that is inserted in the strap portion, thus preventing strap portion damage, which otherwise might occur when moving the ends of the connection pin portion to fit or release the connection pin portion into/from the body.

According to embodiments of the present disclosure, the holder portion of the wearable device includes the guide hole for guiding the knob, which leads to easier insertion of the connection pin portion into the body and the strap portion while facilitating coupling/decoupling between the strap portion and the body through the connection pin portion. The holder portion has the stopper portions that constrains the movement of the connection pin portion, contributing to a stable coupling between the strap portion and the body.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIGS. 11A-11E is a view illustrating the operation of removing a strap portion from a body portion and inserting another into the body portion, according to an embodiment of the present disclosure;

Throughout the drawings, it should be noted that like reference numbers are used to depict the same or similar elements, features, and structures.

DETAILED DESCRIPTION

Figure 1:
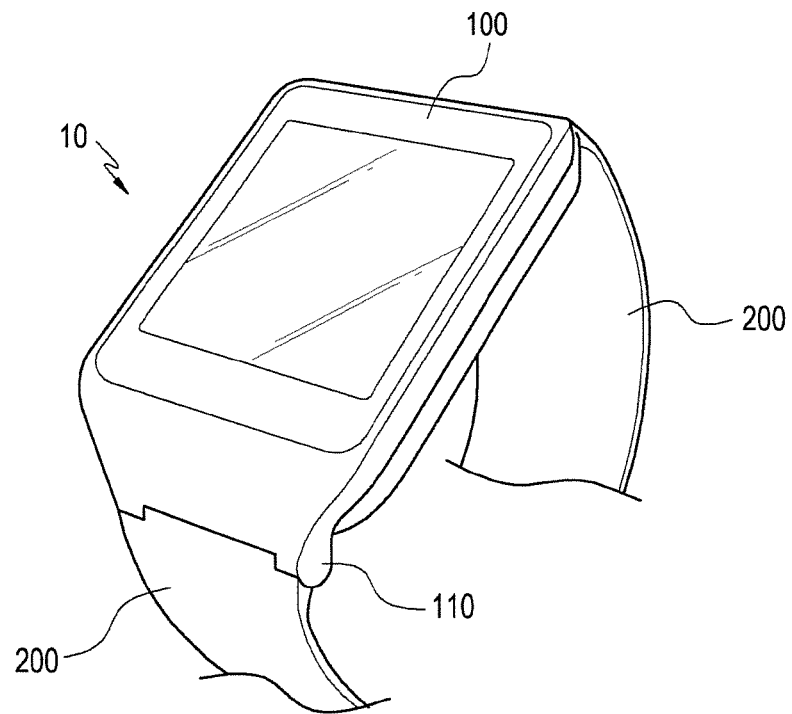
FIG. 1 is a perspective view illustrating a wearable device according to an embodiment of the present disclosure.

FIGS. 1 through 14, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged electronic device. Various changes may be made to the present disclosure, and the present disclosure may come with a diversity of embodiments. Some embodiments of the present disclosure are shown and described in connection with the drawings.

However, it should be appreciated that the present disclosure is not limited to the embodiments, and all changes and/or equivalents or replacements thereto also belong to the scope of the present disclosure.

The terms such as 'first' and 'second' may be used to denote various components, but the components are not limited by the terms.

The terms are used only to distinguish one component from another.

For example, a first component may be denoted a second component, and vice versa without departing from the scope of the present disclosure.

The term 'and/or' may denote any or combination(s) of a plurality of related items as listed.

The terms 'front,' 'rear,' 'upper,' and 'lower,' which are relative ones for denoting their respective components as viewed in the drawings, may be replaced with 'first,' 'second,' 'third,' and 'fourth,' respectively.

The order denoted by the ordinal numbers, first and second, may be varied as necessary.

The terms as used herein are provided merely to describe some embodiments thereof, but not to limit the present disclosure.

It is to be understood that the singular forms "a," "an," and "the" include plural references unless the context clearly dictates otherwise.

It will be further understood that the terms "comprise" and/or "have," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art to which the embodiments of the present disclosure belong.

It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the term "wearable device" denotes any electronic device that can be worn on the user's wrist, including, but not limited to, a typical type of analog or digital wristwatch, a smartwatch, and a bio signal measuring device.

The wearable device communicates with an external electronic device, e.g., a server or performs tasks by interworking with such an external electronic device.

For example, the wearable device can transmit images captured by its camera and/or location information detected by its sensor to the server via a network and can store and display data transmitted to an electronic device interworking therewith.

The network includes, but is not limited to, a mobile or cellular communication network, a local area network (LAN), a wireless local area network (WLAN), a wide area network (WAN), the Internet, or a small area network (SAN).

The electronic device interworking with the wearable device can be a smartphone, a mobile phone, a navigation device, a game device, a TV, a head unit for vehicles, a laptop computer, a tablet computer, a personal media player (PMP), or a personal digital assistant (PDA).

In certain embodiments, the electronic device is implemented as a pocket-sized portable communication terminal with a radio communication function.

The electronic device can be a flexible device or a flexible display.

Specifically, according to an embodiment of the present disclosure, when the wearable device includes a smartwatch or a bio signal measuring device, a network environment associated with the wearable device and the operation and structure of the processor of the wearable device are described with reference to FIGS. 12 to 14.

Certain embodiments of a wearable device are now described with reference to FIGS. 1 through 4.

FIG. 1 is a perspective view illustrating a wearable device according to an embodiment of the present disclosure.

The wearable device 10 includes a body portion 100, a strap portion 200, and a connection module that includes a holder portion 300 and a connection pin portion 400. The wearable device 10 can be an analog or digital watch, a smartwatch, or a wearable bio signal measuring device.

The body portion 100 is the main body of an analog or digital wrist watch, including a module for a wearable electronic device having a displaying function or other multiple functions, or a module for sensing bio signals or the user's movement. In certain embodiments, the display of the wearable electronic device is incorporated with a touch panel to be utilized as an input device. The bio signal sensing module includes a sensor for sensing the user's movement or an electrode pad for measuring the user's heartbeat.

Figure 2:
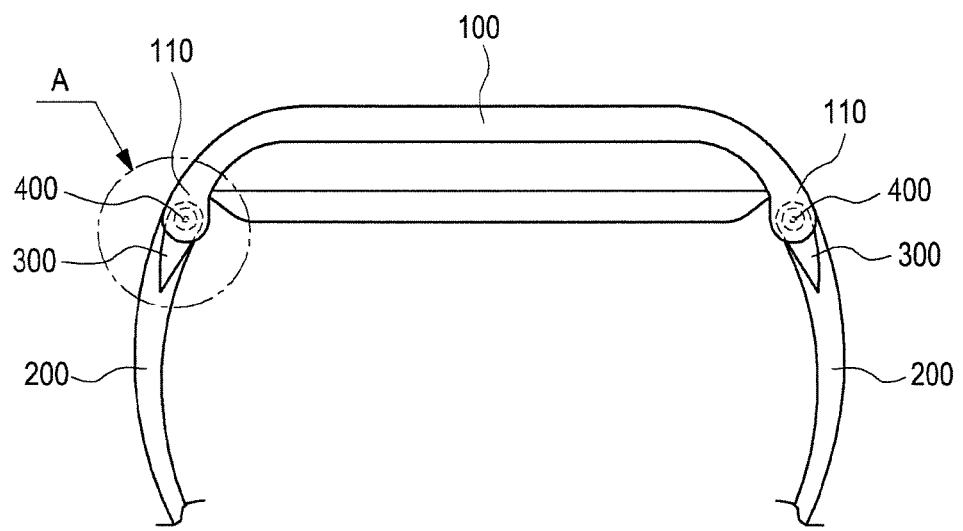
FIG. 2 is a cross-sectional view illustrating a wearable device according to an embodiment of the present disclosure.
Figure 3:
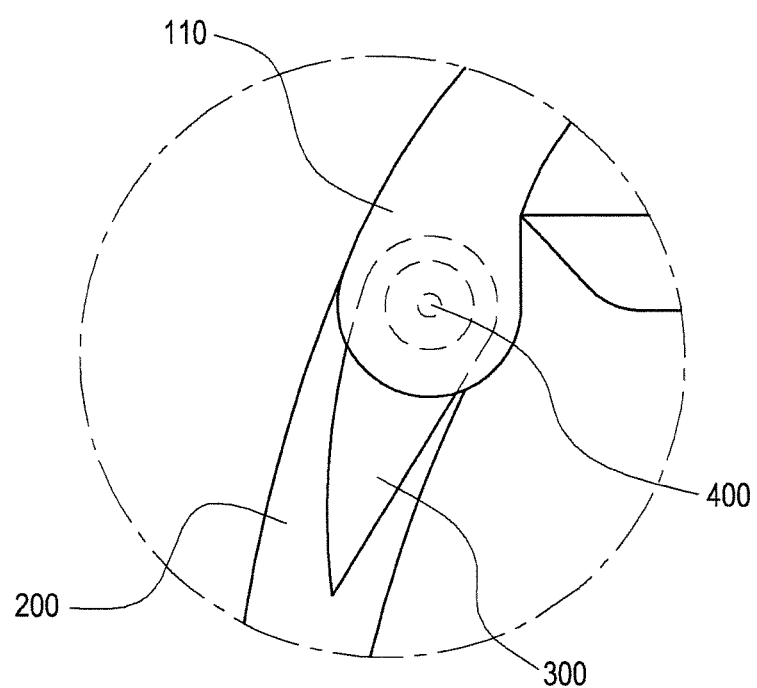
FIG. 3 is an expanded cross-sectional view illustrating a wearable device with a connection module positioned between a body and a strap portion to couple the body with the strap portion, according to an embodiment of the present disclosure.
Figure 4:
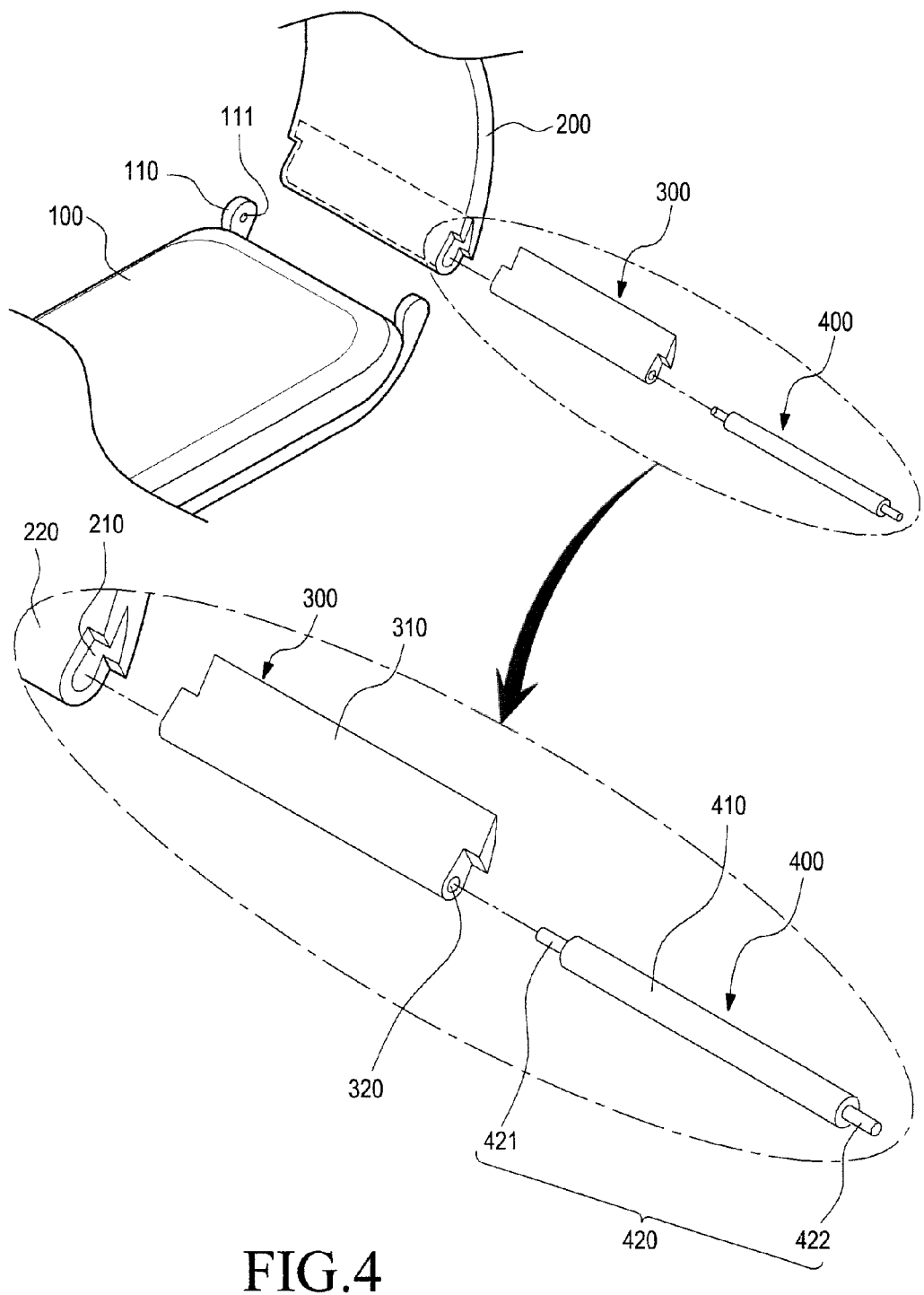
FIG. 4 is an exploded perspective view illustrating a wearable device according to an embodiment of the present disclosure.

FIG. 2 is a cross-sectional view illustrating a wearable device according to an embodiment of the present disclosure. FIG. 3 is an expanded cross-sectional view illustrating a wearable device with a connection module positioned between a body and a strap portion to couple the body with the strap portion, according to an embodiment of the present disclosure. FIG. 4 is an exploded perspective view illustrating a wearable device according to an embodiment of the present disclosure.

Referring to FIGS. 2 to 4, the body portion 100 includes a strap coupler portion 110 for coupling the strap portion 200, described below, at opposite positions around the body portion 100. Although the strap coupler portion 110 is included in the body portion 100, embodiments of the present disclosure are not limited thereto. For example, a separate bezel member (not shown) can be provided to surround the body portion 100 along an outer edge of the body portion 100, and the strap coupler portions 110 can be provided to face each other around the bezel member. The strap coupler portion 110 includes other various positions, structures, or shapes as long as the strap coupler portion 110 couples the strap portion 200 to the body portion 100. A pair of strap coupler portion 110 is provided at two opposite ends, respectively, of the body portion 100. The strap coupler portion 110 includes a pair of coupling protrusions. Pin holes 111, respectively, are provided in the respective first surfaces of the pair of coupling protrusions facing each other. Two opposite ends of a connection pin portion 400, which is described below, are fitted into the pin holes 111, respectively, fastening the connection pin portion 400.

The strap portion 200 is coupled to the body portion 100, specifically to the strap coupler portion 110, and the strap portion 200 and the body portion 100 are put on the user's body.

According to an embodiment of the present disclosure, a pair of straps 200 are provided, which may be respectively referred to as a first band and a second band. Two strap coupler portions 110, respectively, are provided at two opposite ends of the body portion 100, and the two strap coupler portions 110 are hereinafter referred to as a first strap coupler portion and a second strap coupler portion, respectively. The first band and the second band are coupled to the first strap coupler portion 110 and the second strap coupler portion 110, respectively. For example, an end of the first band and an end of the second band are coupled with the first strap coupler portion 110 and the second strap coupler portion 110, respectively. Respective second ends of the first band and the second band, respectively, have a coupling member and a coupling hole corresponding to the coupling member. When the coupling member is coupled into the coupling hole, the wearable device can be put on the user's wrist. However, the structure for coupling the second ends of the first band and the second band is not limited thereto, and any other types of coupling structures could be used as long as they are able to couple the second ends of the first band and the second band so that the user can wear the wearable device.

According to an embodiment of the present disclosure, the strap portion 200 includes a seating opening 210. The seating opening 210 is formed through an end of the strap 200, where the strap 200 is coupled to the strap coupler portion 110 of the body portion 100—hereinafter, the end of the strap portion 200 is referred to as an engagement part. A holder portion 300, which is described below, is inserted into the seating opening 210. The seating opening 210 passes through the engagement part from a side to another, and the seating opening 210 fastens the holder body 310 of the holder portion 300, with the holder portion 300 placed in the seating opening 210.

According to an embodiment of the present disclosure, the strap portion 200 is formed of urethane rubber, silicone rubber, carbon, leather, or fabric, or the strap portion 200 includes a carbon band obtained by applying or processing carbon to the listed material.

The connection module including the holder portion 300 and the connection pin portion 400 is positioned between the body portion 100 and the strap portion 200, specifically, the engagement part of the strap portion 200, to couple the engagement part of the strap portion 200 to the strap coupler portion 110 of the body portion 100. The connection module, includes a connection pin portion 400 coupling the strap portion 200 with the body portion 100 and a holder portion 300 having a coupling space for the connection pin portion 400 and reinforcing the strap portion 200 when the strap portion 200 is coupled with the body portion 100 by the connection pin portion 400.

The holder portion 300 backs up the engagement part of the strap portion 200. The holder portion 300 is provided for an easy and stable coupling of the connection pin portion 400 as well. According to an embodiment of the present disclosure, the holder portion 300 includes a holder body 310 and a pin mounted hole 320.

The holder body 310 is inserted into the seating opening 210. According to an embodiment of the present disclosure, the holder body 310 is shaped in cross section, like a fan or a cross section of an airplane wing, so that the hold body 310 surface slims down away from the engagement part of the strap portion 200. The holder body 310 is provided to be engaged and fastened in the seating opening 210. The holder body 310 is formed of a resin or other plastics, such as by, for example, injection molding.

The pin mounted hole 320 passes through the holder body 310 from an end to another. The connection pin portion 400 is inserted into the pin mounted hole 320 to enable a coupling between the body portion 100 and the holder portion inserted strap portion 200, specifically the strap coupler portion 110. The pin mounted hole 320 can have the same or similar size as the pin body 410 to allow for insertion of the pin body 410, which is described below.

The connection pin portion 400 is inserted into the holder portion 300, specifically the pin mounted hole (or via) 320, to couple the strap portion 200 with the body portion 100. According to an embodiment of the present disclosure, the connection pin portion 400 includes a pin body 410 and first and second protrusions 421 and 422 sticking out respectively from both ends of the pin body 410 and fitted/removed into/from the pin holes 111.

The holder portion 300 can be inserted in the strap portion 200, with the pin body 410 placed in the holder portion 300. The pin body 410 can pass through the pin mounted hole 320 from an end to another, and the pin body 410 is shaped as an arm. The pin body 410 can be fitted into the pin mounted hole 320.

The first and second protrusions 421 and 422 are fitted into or removed from the pin holes 111 of the strap coupler portion sticking out from two opposite ends of the pin body 410. The first protrusion 421 or the second protrusion 422 is elastically supported by an elastic body 440, such as a spring, provided inside the pin body 410.

As such, the holder portion 300, inserted into the engagement part of the strap portion 200 coupled with the body portion 100, provides a support to the engagement part, allowing for a more stable coupling between the strap portion 200 and the body portion 100.

A wearable device 10 is now described with reference to FIGS. 5 to 11, according to an embodiment of the present disclosure. The wearable device 10 is similar in structure to the wearable device described above in connection with FIGS. 1 to 4, and the description thereof primarily focuses on the differences therefrom.

Figure 5:
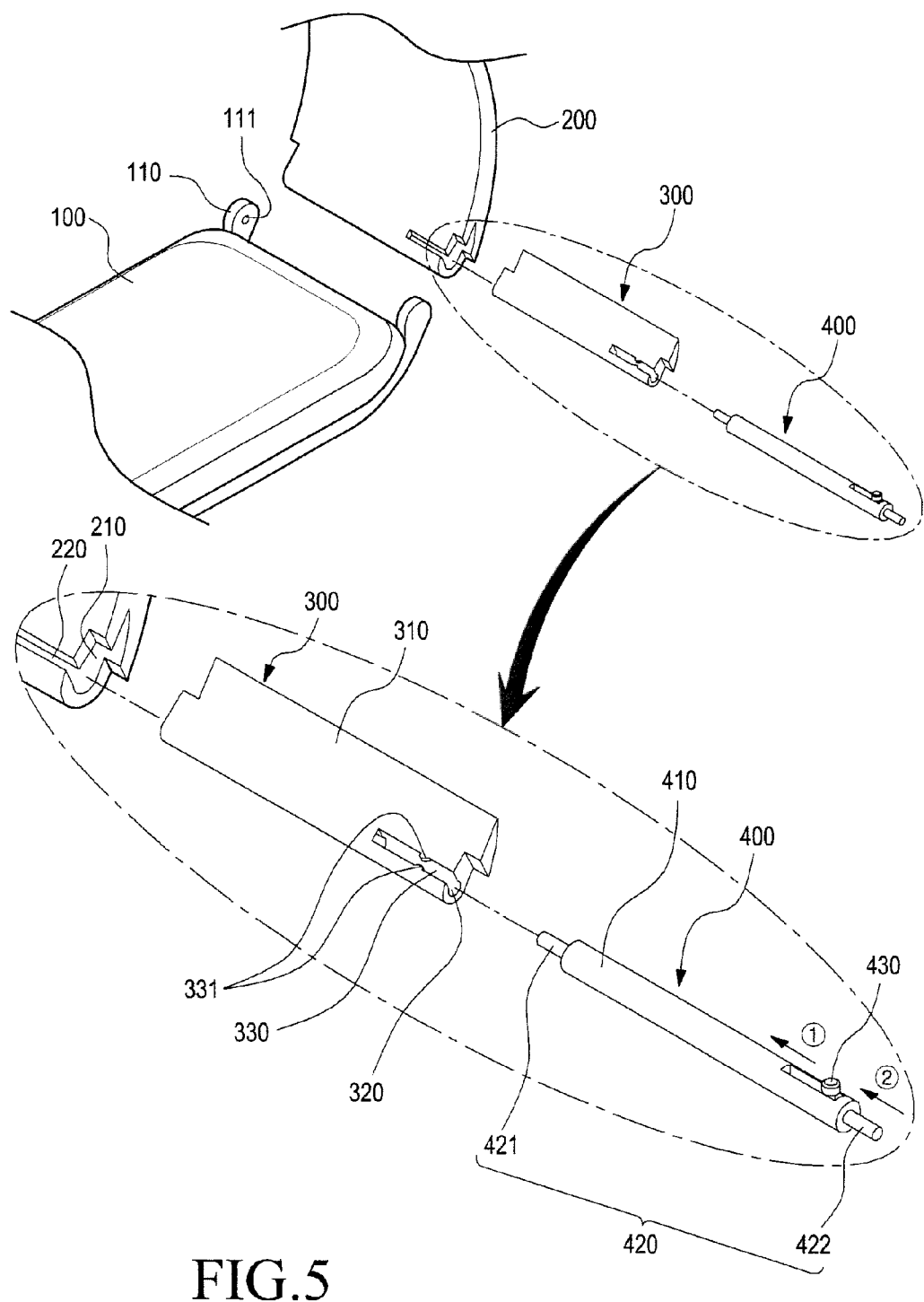
FIG. 5 is an exploded perspective view illustrating a wearable device according to an embodiment of the present disclosure.
Figure 6:
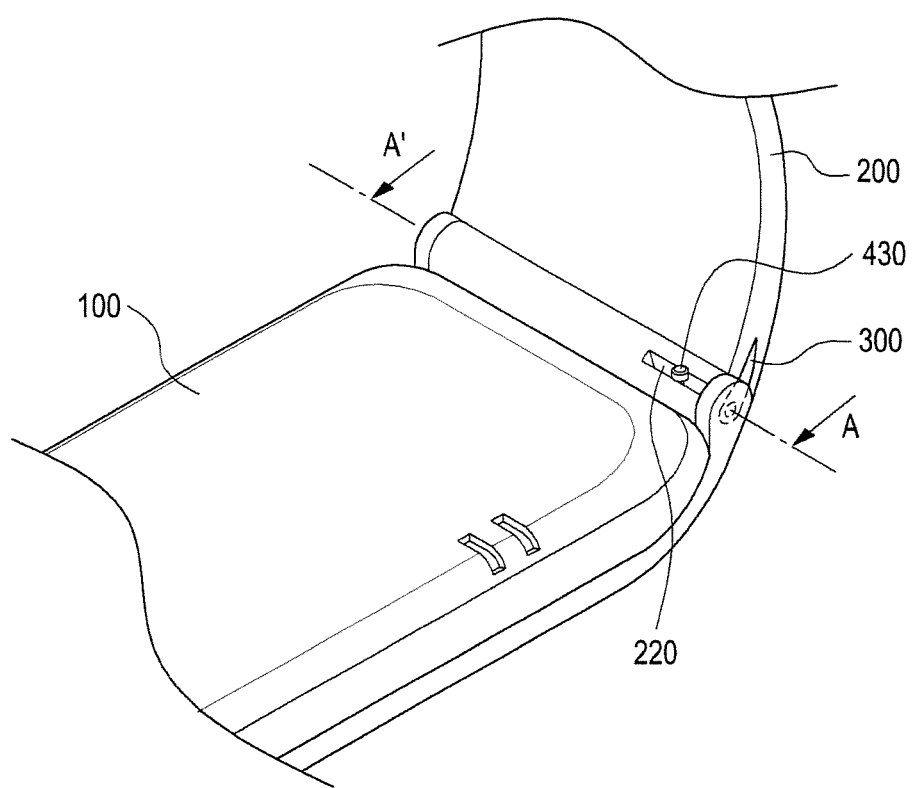
FIG. 6 is a perspective view illustrating a wearable device as assembled, according to an embodiment of the present disclosure.
Figure 7A:
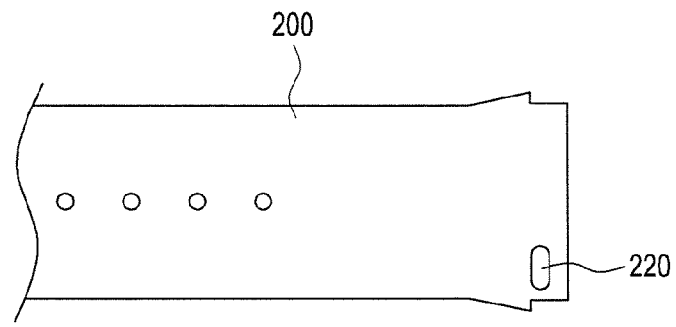
FIGS. 7A and 7B is a rear view illustrating a strap portion of a wearable device according to an embodiment of the present disclosure.
Figure 7B:
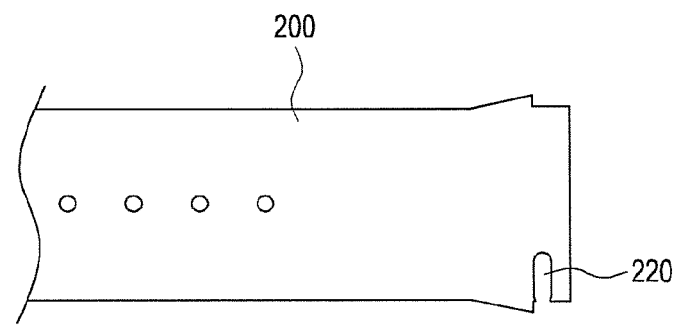

FIG. 5 is an exploded perspective view illustrating a wearable device according to an embodiment of the present disclosure. FIG. 6 is a perspective view illustrating a wearable device as assembled, according to an embodiment of the present disclosure. FIG. 7 is a rear view illustrating a strap portion of a wearable device according to an embodiment of the present disclosure.

Referring to FIGS. 5 to 7, the wearable device 10, which can be similar to the wearable device described above in connection with FIGS. 1 to 4, includes a body portion 100, a strap portion 200, and a connection module, including a holder portion 300 and a connection pin portion 400. The differences between the wearable device 10 are in the presence or absence of an exposure hole 220 in the strap portion 200, the structure of the connection pin portion 400, and the presence or absence of a guide hole 330 in the holder portion 300.

Specifically, the body portion 100 is substantially the same in structure as the body portion 100 described above in connection with FIGS. 1 to 4.

The strap portion 200 is similar to that of the wearable device described above in connection with FIGS. 1 to 4 except that the connection pin portion 400 includes a knob 430 and the engagement part has an exposure hole 220 to expose the knob 430 to the outside of the strap portion 200.

Specifically, the strap portion 200 includes a seating opening 210 and an exposure hole 220.

The seating opening 210 is provided at an end of the strap portion 200, specifically at the engagement part of the strap portion 200. A holder portion 300, which is described below, can be inserted into the seating opening 210. The seating opening 210 passes through the engagement part from an end to another. The holder body 310 of the holder portion 300 is placed and fastened in the seating opening 210.

The exposure hole 220 is an opening that is positioned in the strap portion 200 of the coupled portion and passes from the surface of the strap portion 200 to the seating opening 210. The exposure hole 220 can be provided corresponding to a side of the coupled portion, specifically, the portion where the knob of the connection pin portion 400, which is described below, is positioned, and the exposure hole 220 allows the knob 420 to be exposed to a rear surface of the strap portion 200. The exposure hole 220 is an opening that passes from the rear surface of the strap portion 200 to the seating opening 210 and an opening that, when the holder portion 300, which is described below, is mounted in the seating opening 210, connects through the guide hole 330 of the holder portion 300 up to an inside of the pin mounted hole 320.

According to an embodiment of the present disclosure, the exposure hole 220 has a predetermined distance from a portion of the strap portion 200 to another. Here, the "predetermined distance" is the distance within which the knob may travel to allow the first protrusion 421 or the second protrusion 422 to be fitted into or removed from its corresponding pin hole 111. For example, the exposure hole 220 can have a predetermined length from a side of the strap portion 200 to the other side thereof, which is shaped to be opened to the outside (refer to FIG. 7(b)).

In certain embodiments, the strap portion 200 is formed of urethane rubber, silicone rubber, carbon, leather, or fabric, or the strap portion 200 includes a carbon band obtained by processing the listed material with carbon.

According to an embodiment of the present disclosure, the connection module include a connection pin portion 400 and a holder portion 300, in which the connection pin portion 400 can be inserted. The holder portion 300 is positioned between the body portion 100 and the strap portion 200, specifically the engagement part of the strap portion 200, with the holder portion 300 inserted in the holder portion 300, so as to couple the engagement part of the strap portion 200 into the strap coupler portion 110 of the body portion 100.

Figure 8:
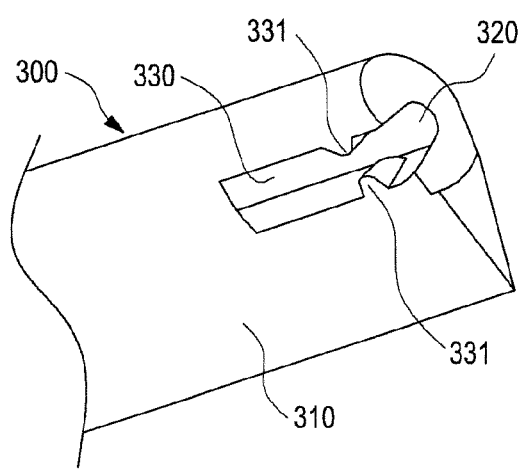
FIG. 8 is a perspective view illustrating a holder portion of a wearable device according to an embodiment of the present disclosure.
Figure 9:
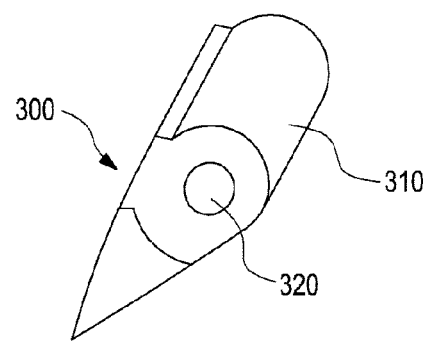
FIG. 9 is a perspective view illustrating a holder portion of a wearable device as viewed in a different direction, according to an embodiment of the present disclosure.

FIG. 8 is a perspective view illustrating a holder portion of a wearable device according to an embodiment of the present disclosure. FIG. 9 is a perspective view illustrating a holder portion of a wearable device as viewed in a different direction, according to an embodiment of the present disclosure.

According to an embodiment of the present disclosure, the holder portion 300 is engagingly seated in the seating opening 210 and provides a space for the connection pin portion 400 to couple the strap portion 200 with the body portion 100, reinforcing the coupled portion of the strap portion 200. In other words, the holder portion 300 can back up the coupled portion of the strap portion 200, while providing an easy and stable coupling between the strap portion 200 and the body portion 100 through the connection pin portion 400.

The holder portion 300 has a holder body 310, a pin mounted hole 320, and a guide hole 330, which makes it distinct from the holder portion 300 described above in connection with FIGS. 1 to 4.

The holder body 310 is inserted into the seating opening 210. The holder body 310 can be shaped in cross section like a fan or a cross section of an airplane wing that slims down away from the engagement part of the strap portion 200. The holder body 310 is provided to be engagingly fastened in the seating opening 210. The holder body 310 is formed of a resin or other plastics by, e.g., injection molding.

The pin mounted hole 320 passes through the holder body 310 from an end to another, and the connection pin portion 400 is inserted into the pin mounted hole 320 to couple the body portion 100 with the holder portion inserted strap portion 200, specifically the strap coupler portion 110. The pin mounted hole 320 can have the same or similar size to the pin body 410 so as to allow the pin body 410 to be inserted into the pin mounted hole 320.

Figure 10:
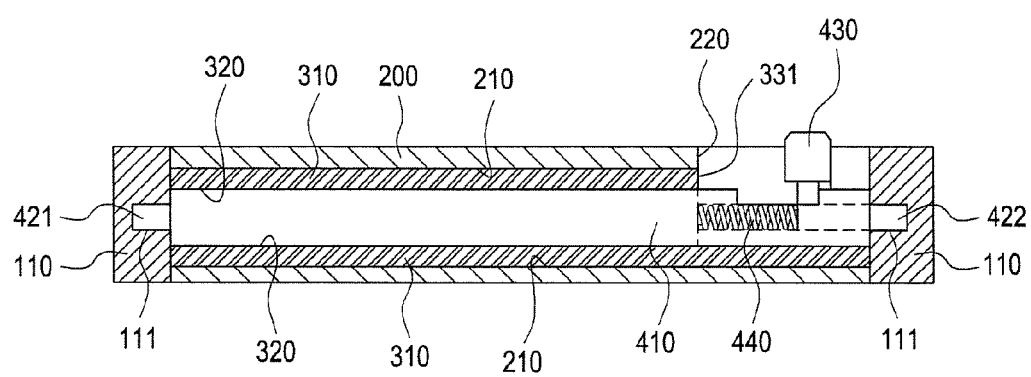
FIG. 10 is a cross-sectional view taken along line A-A' of FIG. 6.

FIG. 10 is a cross-sectional view taken along line A-A' of FIG. 6.

Referring to FIG. 10, the knob of the connection pin portion 400 to be inserted in the pin mounted hole 320 is seated in the guide hole 330, and the guide hole 330 are formed to be exposed to a surface of the strap portion 200. Specifically, the guide hole 330 is an opening that is formed at a position corresponding to the exposure hole 220 detailed above to connect to the exposure hole 220 and passes through the inside of the pin mounted hole 320. A side of the guide hole 330 is formed to be opened to a side of the holder body 310. As the side of the guide hole 330 is opened at a side of the holder body 310, the knob 430 protruded from the connection pin portion 400 to be described below can be inserted into the guide hole 330. The guide hole 330 is formed to have a predetermined length in a direction of the other side from the opened side. Here, the "predetermined length" can be provided as a travelling distance of the knob that allows one of the first protrusion 421 or the second protrusion of the connection pin portion 400 to be described below as pulled out from the pin hole 111.

The guide hole 330 is positioned corresponding to the exposure hole 220 and extends to the exposure hole 220 to be opened to the outside of the strap portion 200. The guide hole 330 can be similar in size to the exposure hole 220; and the guide hole 330 and the exposure hole 220 form a travelling distance for the knob 430 of the connection pin portion 400. The knob 430 is inserted along the guide hole 330 and is exposed to the outside of the back surface of the strap portion 200 through the guide hole 330 and the exposure hole 220. The user may move the knob 430 to slide the connection pin portion 400 into and from the body portion 100.

As described supra, the guide hole 330 has an opened end, so that when the connection pin portion 400 is inserted into the pin mounted hole 320, the knob 430 of the connection pin portion 400 can be slid in along the guide hole 330 through the opened end of the guide hole 330.

The knob 430 is able to be removed or fall out of the holder body 310 through the opened end of the guide hole 330. To prevent such removal or extraction, or to restrict the movement of the knob 430, a pair of stopper portions 331 facing each other is provided in the guide hole 330. The knob 430 is press-fittingly inserted into the guide hole 330 through the opened end of the guide hole 330 and the space between the stopper portions 331 and can be thus positioned between the opposite end of the opened end of the guide hole 330 and the stopper portions 331, so that the knob 430 can travel between the opposite side of the guide hole 330 and the stopper portions 331, with the connection pin portion 400 inserted in the pin mounted hole 320.

The connection pin portion 400 differs in structure from the connection pin portion 400 described above in connection with FIGS. 1 to 4.

The connection pin portion 400, similar to that described above in connection with FIGS. 1 to 4, is inserted into the holder portion 300, specifically the pin mounted hole 320, to couple the strap portion 200 with the body portion 100. The connection pin portion 400 includes a pin body 410, first and second protrusions projecting from the pin body 410 and detachably inserted into the pin holes 111, and a knob that makes it distinct from the connection pin portion 400 described above in connection with FIGS. 1 to 4.

The holder portion 300 is positioned inside the strap portion 200, with the pin body 410 inserted in the holder portion 300. The pin body 410 is shaped as an arm penetrating the pin mounted hole 320 from a side to the other side thereof, and the pin body 410 is provided to be inserted and engaged to the pin mounted hole 320.

The first and second protrusions 421 and 422 are fitted into or removed from the pin holes 111 of the strap coupler portion sticking out on two opposite ends of the pin body 410. The first protrusion 421 or the second protrusion 422 is connected with the knob 430 and can be elastically supported by an elastic member 440, e.g., a spring. According to an embodiment of the present disclosure, the second protrusion 422 (hereinafter, referred to as a spring pin 422) is connected with the knob 430, for the purpose of description. However, the first protrusion 421 can be fitted into or removed from the inside of the pin body 410 as well. Alternatively, the first protrusion 421 can be a spring pin depending on the position of the guide hole 330 and the exposure hole 220. When the knob 430 is pulled away from the stopper portions 331, the spring pin 422 can be pushed in along the inside of the pin body 410, and thus, the connection pin portion 400 can be shrunken, subject to the position where the connection pin portion 400 can be unplugged from the pin holes 111 or fitted back into the pin hole 111.

An example of swapping straps is now described with reference to FIG. 11, according to an embodiment of the present disclosure.

FIG. 11 is a view illustrating the operation of removing a strap portion 200 from a body portion 100 and inserting another 200 into the body portion 100, according to an embodiment of the present disclosure.

Referring to FIG. 11, the holder portion 300 is inserted into the strap portion 200 with the connection pin portion 400 positioned inside, and the first protrusion 421 and the spring pin 422 of the connection pin portion 400 are respectively fitted into pin hole 111 of the body portion 100, leaving the body portion 100 and the strap portion 200 to be coupled with each other hole the connection module, which includes the holder portion 300 and the connection pin portion 400 (see FIG. 11(a)). To swap strap portions 200, the user pulls the knob 430, sticking out through the exposure hole 220 on the back surface of the strap portion 200, from a side to another (in the direction indicated by an arrow) (see FIG. 11(a)-1). The knob 430 runs along the guide hole 330, but not beyond the stopper portions 331, preventing damage to the strap portion 200, specifically the engagement part, which otherwise might occur. As the knob 430 moves along, the spring pin 422 connected with the knob 430 can be pushed inside the pin body 410. The spring pin 422 is pulled away from the pin hole 111, allowing the side of the strap portion 200 to be separated from the body portion 100 (see FIG. 11(b)).

The following is an exemplary operation of reinstalling the strap portion 200 to the body portion 100 (refer to FIG. 11(c) to (e)).

The holder portion 300 having the connection pin portion 400 inserted therein remains fastened in the seating opening 210. The first protrusion 421 and the spring fin 422 of the connection pin portion 400 are left sticking out from both sides of the strap portion 200. The first protrusion 421 is fitted into the pin hole 111 (see FIGS. 11(c) and (c)-1). The knob 430 projected through the exposure hole 220 on the back surface of the strap portion 200 is pulled away from the stopper portions 331 (in the direction indicated by an arrow) (see FIG. 11(d)-1), the spring pin 422 is forced into the inside of the pin body 410 (see FIGS. 11(e) and (e)-1). The knob 430 travels along the guide hole 330, but not beyond the stopper portions 331, preventing damage that otherwise might arise. As the spring pin 422 is pushed inside of the pin body 410, the strap portion 200 can be fitted into the strap coupler portion 110. When the knob 430 is released, the knob 430 along with the spring pin 422 is elastically pushed towards the stopper portions 331 by the elastic member 440, leaving the spring pin 422 to spring out of the side of the pin body 410 to fit into the pin hole 111 of the strap coupler portion 110. As such, the strap portion 200 can be easily coupled with the body portion 110.

Figure 12:
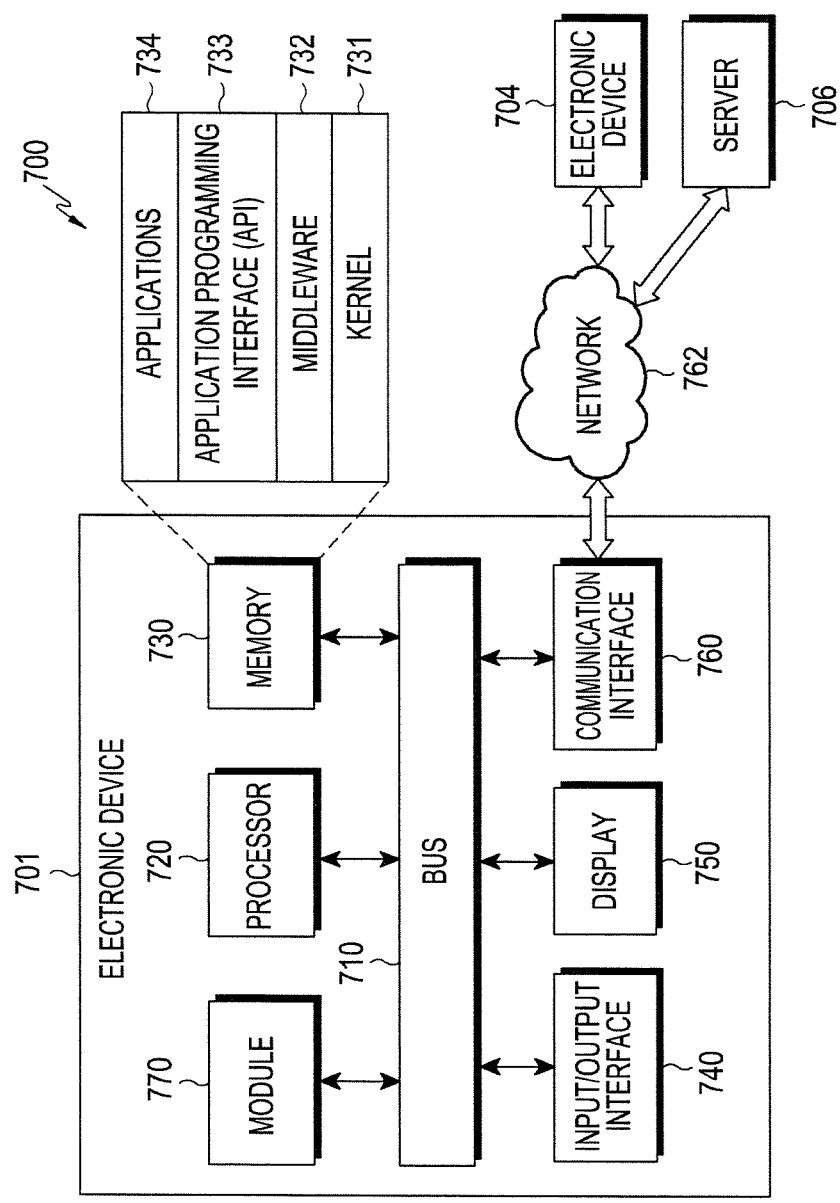
FIG. 12 is a view illustrating a network environment including an electronic device according to an embodiment of the present disclosure.
Figure 13:
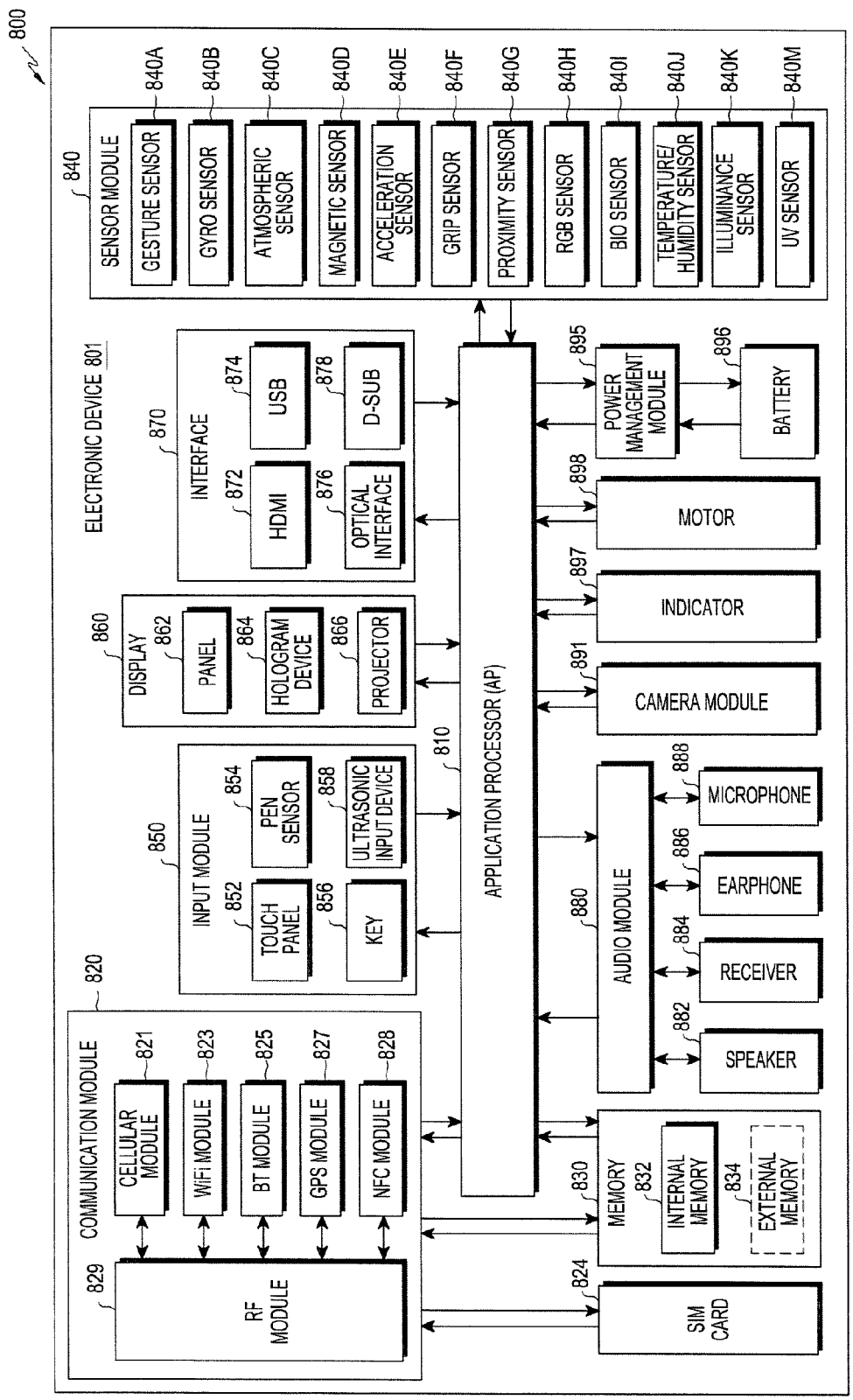
FIG. 13 is a block diagram illustrating an electronic device according to an embodiment of the present disclosure.
Figure 14:
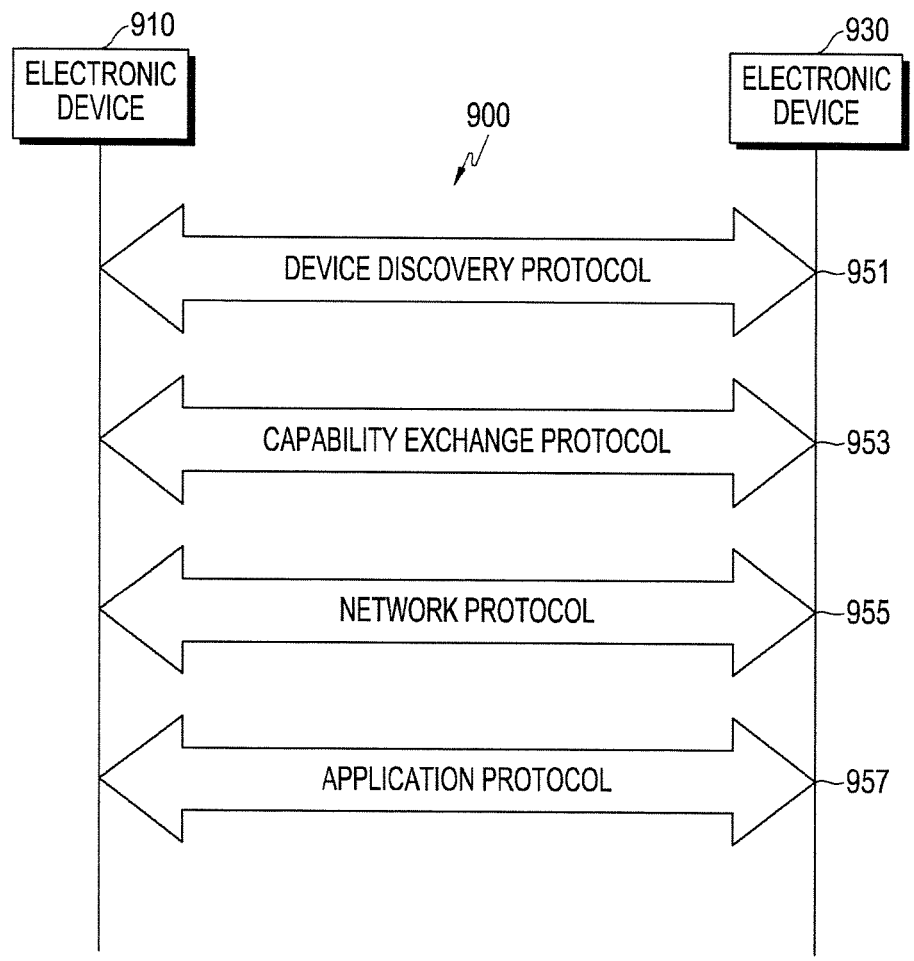
FIG. 14 illustrates communication protocols between a plurality of electronic devices (e.g., a wearable device and an external electronic device) according to an embodiment of the present disclosure.

FIGS. 12 to 14 are views illustrating a network environment associated with a wearable device, the driving processor of the wearable device, and communication protocols for communication with an external electronic device when the wearable device is a smartwatch or bio signal measuring device, according to embodiments of the present disclosure.

FIG. 12 is a view illustrating a network environment including an electronic device according to an embodiment of the present disclosure.

Referring to FIG. 12, the electronic device 701 (which can be a wearable device according to an embodiment of the present disclosure) includes a bus 710, a processor 720, a memory 730, an input/output interface 740, a display 750, a communication interface 760, and other various function modules 770 (e.g., a bio signal measuring module, an ultraviolet (UV) index measuring module, or fingerprint recognition module).

The bus 710 connects the above-listed components to each other, and the bus 110 can carry data (e.g., control messages) between the components.

The processor 720 receives a command from other component (e.g., the memory 730, the input/output interface 740, the display 750, the communication interface 760, or the information providing module 770) through, e.g., the bus 710, interprets the received command, and executes computation or data processing according to the interpreted command.

The memory 730 stores a command or data received from other component (e.g., the input/output interface 740, the display 750, the communication interface 760, or the information providing module 770) or a command or data generated by the processor 720 or other component.

The memory 730 includes programming modules including, e.g., a kernel 731, middleware 732, an application programming interface (API) 733, or an application 734.

The programming modules can be configured in software, firmware, hardware or a combination of two or more thereof.

The kernel 731 controls or manages system resources (e.g., the bus 710, the processor 720, or the memory 730) used to execute the operation or function implemented in the other programming modules, e.g., the middleware 732, the API 733 or the application 734.

The kernel 731 provides an interface that allows the middleware 732, the API 733, or the application 734 to access the individual components of the electronic device 701 to control or manage the same.

The middleware 732 functions as a relay to allow the API 733 or the application 734 to communicate data with the kernel 731.

A plurality of applications 734 can be provided. The middleware 732 controls work requests received from the applications 734, e.g., by allocation the priority of using the system resources of the electronic device 701 (e.g., the bus 710, the processor 720, or the memory 730) to at least one of the plurality of applications 134.

The API 733 is an interface allowing the application 734 to control functions provided from the kernel 731 or the middleware 732. For example, the API 733 includes at least one interface or function (e.g., a command) for filing control, window control, image processing or text control.

According to an embodiment of the present disclosure, there can be provided a plurality of applications 734 including an SMS/MMS application, an email application, a calendar application, an alarm application, a healthcare application (e.g., an application for measuring exercise amount or blood sugar), or an environmental information application (e.g., an application providing atmospheric pressure, moisture, or temperature information).

Additionally or alternatively, the application 734 can be an application related to information exchange between the electronic device 701 and an external electronic device (e.g., electronic device 704).

Examples of the information exchange-related application include, but are not limited to, a notification relay application for transferring specific information to the external electronic device, or a device management application for managing the external electronic device.

For example, the notification relay application includes a function for relaying notification information generated from other applications of the electronic device 701 (e.g., the SMS/MMS application, email application, healthcare application, or environmental information application) to the external electronic device (e.g., the electronic device 704).

Additionally or optionally, the notification relay application receives notification information from, e.g., the external electronic device (e.g., the electronic device 704) and provides the received notification information to the user.

The device management application performs at least some functions of the external electronic device (e.g., the electronic device 704) communicating with the electronic device 701 (for example, turning on/off the external electronic device (or some components of the external electronic device) or control of brightness (or resolution) of the display), and the device management application manages (e.g., install, delete, or update) an application operating in the external electronic device or a service (e.g., call service or message service) provided from the external electronic device.

According to an embodiment of the present disclosure, the application 734 includes an application designated depending on the attribute (e.g., type of electronic device) of the external electronic device (e.g., the electronic device 704).

For example, in case the external electronic device is an MP3 player, the application 734 can include an application related to playing music.

Similarly, in case the external electronic device is a mobile medical device, the application 734 includes an application related to healthcare.

According to an embodiment of the present disclosure, the application 734 includes an application designated to the electronic device 701 or an application received from an external electronic device (e.g., a server 706 or the electronic device 704).

The input/output interface 740 transfers commands or data input by the user through an input/output device (e.g., a keyboard or touchscreen) to the processor 720, the memory 730, or the communication interface 770 through, e.g., the bus 710.

For example, the input/output interface 740 can provide data regarding the user's touch input through a touchscreen to the processor 720.

The input/output interface 740 can output, through the input/output device (e.g., a speaker or display), commands or data received from the processor 720, the memory 730, the communication interface 760, or the module 770 through, e.g., the bus 710.

For example, the input/output interface 740 can output voice data processed by the processor 720 to the user through a speaker.

The display 750 displays various types of information (e.g., multimedia data or text data) to the user.

The communication interface 760 enables communication between the electronic device 701 and an external electronic device (e.g., the electronic device 704 or the server 706).

For example, the communication interface 760 connects with the network 762 through a wireline or wireless communication link to communicate with the external electronic device.

The wireless connection can be made by various radio communication protocols, including, but not limited to, wireless fidelity (WiFi), BLUETOOTH® (BT), near field communication (NFC), global positioning system (GPS), or cellular communication protocols (e.g., LTE, LTE-A, CDMA, WCDMA, UMTS, WiBro or GSM).

The wired connection can be made by various wired communication protocols, including, but not limited to, universal serial bus (USB), high definition multimedia interface (HDMI), recommended standard (RS) 232, or plain old telephone service (POTS).

According to an embodiment of the present disclosure, the network 762 is a telecommunication network.

The telecommunication network includes a computer network, the Internet, an Internet of things (IoT) network, or a telephone network.

According to an embodiment of the present disclosure, protocols for communication between the electronic device 701 and the external electronic device (examples of such protocols include, but not limited to, transport layer protocol, data link layer protocol, or physical layer protocol) can be supported by the application 734, the API 733, the middleware 732, the kernel 731, or the communication interface 760.

FIG. 13 is a block diagram illustrating an electronic device 801 according to an embodiment of the present disclosure.

The electronic device 801 includes the whole or part of the configuration of, e.g., the electronic device 701 shown in FIG. 12.

Referring to FIG. 13, the electronic device 801 includes one or more application processors (APs) 810, a communication module 820, a subscriber identification module (SIM) card 824, a memory 830, a sensor module 840, an input device 850, a display 860, an interface 870, an audio module 880, a camera module 891, a power management module 895, a battery 896, an indicator 897, and a motor 898.

The AP 810 controls multiple hardware and software components connected to the AP 810 by running an operating system or application programs, and the AP 810 processes and computes various data including multimedia data.

In certain embodiments, the AP 810 is implemented in, e.g., a System on Chip (SoC).

According to an embodiment of the present disclosure, the AP 810 further includes a graphic processing unit (GPU) (not shown).

The communication module 820 (e.g. the communication interface 760) performs data communication with other electronic devices (e.g., the electronic device 704 or the server 706) connected with the electronic device 801 (e.g., the electronic device 701) via a network.

According to an embodiment of the present disclosure, the communication module 820 includes a cellular module 821, a WiFi module 823, a BT module 825, a GPS module 827, an NFC module 828, and a radio frequency (RF) module 829.

The cellular module 821 provides voice call, video call, text, or Internet services through a communication network (e.g., an LTE, LTE-A, CDMA, WCDMA, UMTS, WiBro, or GSM network).

The cellular module 821 performs identification and authentication on the electronic device in the communication network using, e.g., a subscriber identification module (e.g., the SIM card 824).

According to an embodiment of the present disclosure, the cellular module 821 performs at least some of the functions providable by the AP 810.

For example, the cellular module 821 performs at least some of the multimedia control functions.

According to an embodiment of the present disclosure, the cellular module 821 includes a communication processor (CP).

In certain embodiments, the cellular module 821 is implemented in, e.g., an SoC.

Although in FIG. 13 the cellular module 821 (e.g., a communication processor), the memory 830, or the power management module 895 are provided separately from the AP 810, the AP 810 is configured to include at least some (e.g., the cellular module 821) of the above-listed components, according to an embodiment of the present disclosure.

According to an embodiment of the present disclosure, the AP 810 or the cellular module 821 (e.g., a communication processor) loads commands or data received from a non-volatile memory or other component connected thereto and process the loaded commands or data.

The AP 810 or the cellular module 821 stores, in the non-volatile memory, data received from other component(s) or data generated by the other component(s).

The WiFi module 823, the BT module 825, the GPS module 827, or the NFC module 828 includes a process for, e.g., processing data communicated through the module.

Although in FIG. 13 the cellular module 821, the WiFi module 823, the BT module 825, the GPS module 827, and the NFC module 828 are shown in their respective separate blocks, at least some (e.g., two or more) of the cellular module 821, the WiFi module 823, the BT module 825, the GPS module 827, and the NFC module 828 are included in a single integrated circuit (IC) or an IC package.

For example, at least some of the processors respectively corresponding to the cellular module 821, the WiFi module 823, the BT module 825, the GPS module 827, and the NFC module 828 (e.g., the communication processor corresponding to the cellular module 821 and the WiFi processor corresponding to the WiFi module 823) can be implemented in a single SoC.

In certain embodiments, the RF module 829 communicates data, e.g., RF signals.

The RF module 829 includes, e.g., a transceiver, a power amp module (PAM), a frequency filter, or a low noise amplifier (LNA) (not shown).

The RF module 829 further includes parts (e.g., conductors or wires) for communicating radio waves in a free space upon performing wireless communication.

Although in FIG. 13 the cellular module 821, the WiFi module 823, the BT module 825, the GPS module 827, and the NFC module 828 share a single RF module 829, the cellular module 821, the WiFi module 823, the BT module 825, the GPS module 827, or the NFC module 828 may communicate RF signals through a separate RF module(s).

The SIM card 824 includes a subscriber identification module, and the SIM card 2024 cam be inserted into a slot formed at a predetermined position of the electronic device.

The SIM card 824 contains unique identification information (e.g., an integrated circuit card identifier (ICCID) or subscriber information (e.g., an international mobile subscriber identity (IMSI)).

The memory 830 (e.g., the memory 730) includes an internal memory 832 or an external memory 834.

The internal memory 832 includes, e.g., a volatile memory (e.g., a dynamic RAM (DRAM), a static RAM (SRAM), a synchronous dynamic RAM (SDRAM), etc.) or a non-volatile memory (e.g., a one time programmable ROM (OTPROM), a programmable ROM (PROM), an erasable and programmable ROM (EPROM), an electrically erasable and programmable ROM (EEPROM), a mask ROM, a flash ROM, a NAND flash memory, or a NOR flash memory).

According to an embodiment of the present disclosure, the internal memory 832 is a solid state drive (SSD).

The external memory 834 includes a flash drive, e.g., a compact flash (CF) memory, a secure digital (SD) memory, a micro-SD memory, a min-SD memory, an extreme digital (xD) memory, or a memory Stick™.

The external memory 834 can be functionally connected with the electronic device 801 via various interfaces.

According to an embodiment of the present disclosure, the electronic device 801 further includes a storage device (or storage medium) such as a hard disk drive.

The sensor module 840 measures a physical quantity or detects an operational stage of the electronic device 801, and the sensor module 2040 converts the measured or detected information into an electrical signal.

The sensor module 840 includes, e.g., a gesture sensor 840A, a gyro sensor 840B, an atmospheric pressure sensor 840C, a magnetic sensor 840D, an acceleration sensor 840E, a grip sensor 840F, a proximity sensor 840G, a color sensor 840H (e.g., a Red-Green-Blue (RGB) sensor), a bio sensor 840I, a temperature/humidity sensor 840J, an illumination sensor 840K, or an Ultra Violet (UV) sensor 840M.

Additionally or alternatively, the sensor module 840 includes, e.g., an E-nose sensor, an electromyography (EMG) sensor, an electroencephalogram (EEG) sensor, an electrocardiogram (ECG) sensor, an infrared (IR) sensor, an iris sensor, or a finger print sensor which is not shown in the drawings.

The sensor module 840 further includes a control circuit for controlling at least one or more of the sensors included in the sensor module 840.

The input unit 850 includes a touch panel 852, a (digital) pen sensor 854, a key 856, or an ultrasonic input device 858.

The touch panel 852 recognizes touch inputs in at least one of capacitive, resistive, infrared, or ultrasonic methods.

The touch panel 852 further includes a control circuit.

With the capacitive method, physical contact or proximity detection may be possible.

The touch panel 852 further includes a tactile layer.

In this regard, the touch panel 852 provides the user with a tactile response.

The (digital) pen sensor 854 can be implemented in a way identical or similar to e.g., how a touch input of a user is received, or by using a separate sheet for recognition.

The key 856 includes e.g., a physical button, optical key or key pad.

The ultrasonic input device 858 uses an input tool that generates an ultrasonic signal and enables the electronic device 801 to determine data by sensing the ultrasonic signal to the microphone 888, thereby enabling wireless recognition.

According to an embodiment of the present disclosure, the electronic device 801 receives the user's input from an external electronic device (e.g., a network, computer, or server) connected with the electronic device 801 using the communication module 820.

The display 860 (corresponding to the display 750 of FIG. 1) includes a panel 862, a hologram device 864, or a projector 866.

The panel 862 can be, e.g., a Liquid Crystal Display (LCD), Active Matrix Organic Light Emitting Diodes (AMOLEDs), or the like.

The panel 862 can be implemented to be flexible, transparent, or wearable.

The panel 862 also can be incorporated with the touch panel 852 in a module.

The hologram device 864 makes three dimensional (3D) images (holograms) in the air by using light interference.

The projector 866 displays an image by projecting light onto a screen.

The screen can be, for example, located inside or outside of the electronic device 801.

In accordance with an embodiment, the display 860 further includes a control circuit to control the panel 862, the hologram device 864, or the projector 866.

The interface 870 includes e.g., a high definition multimedia interface (HDMI) 872, a (universal serial bus (USB) 874, an optical interface 876, or a D-subminiature (D-sub) 878.

The interface 870 can be included in e.g., the communication interface 760 shown in FIG. 12.

Additionally or alternatively, the interface 870 includes a mobile high-definition link (MHL) interface, a secure digital (SD) card/multimedia card (MMC) interface, or infrared data association (IrDA) standard interface.

The audio module 880 performs various processes (e.g., encoding or decoding) relating to converting a sound wave and audio signal to an electric signal or vice versa.

At least a part of the audio module 880 can be included in, e.g., the input/output interface 740 as shown in FIG. 12.

The audio module 880 processes sound information input or output through e.g., a speaker 882, a receiver 884, an earphone 886, or a microphone 888.

The camera module 891 is a device for capturing still images and videos, and includes, according to an embodiment of the present disclosure, one or more image sensors (e.g., front and back sensors) (not shown), a lens (not shown), an Image Signal Processor (ISP) (not shown), or a flash such as an LED or xenon lamp (not shown).

The power manager module 895 manages power of the electronic device 801.

Although not shown, e.g., a power management integrated Circuit (PMIC), a charger IC, or a battery or fuel gauge is included in the power manager module 895.

The PMIC is mounted on e.g., an IC or an SOC.

A charging method is divided into wired and wireless charging methods.

The charger IC charges a battery and prevents overvoltage or overcurrent from being induced from a charger.

According to an embodiment of the present disclosure, the charger IC is used in at least one of a cable charging scheme and a wireless charging scheme.

The wireless charging scheme includes e.g., a magnetic resonance scheme, a magnetic induction scheme, or an electromagnetic wave based scheme, and an additional circuit, such as a coil loop, a resonance circuit, a rectifier, or the like can be added for wireless charging.

The battery gauge measures an amount of remaining power of the battery 896, a voltage, a current, or a temperature while the battery 896 is being charged.

The battery 896 saves or generates electricity, and supplies power to the electronic device 801 with the saved or generated electricity.

The battery 896 includes, e.g., a rechargeable battery or a solar battery.

The indicator 897 indicates a particular state of the electronic device 801 or a part of the electronic device (e.g., the AP 810), including e.g., a booting state, a message state, or recharging state.

The motor 898 converts an electric signal to a mechanical vibration.

Although not shown, a processing unit for supporting a mobile TV, such as a GPU may be included in the electronic device 801.

The processing unit for supporting mobile TV processes media data conforming to a standard for digital multimedia broadcasting (DMB), digital video broadcasting (DVB), or media flow.

Each of the aforementioned components of the electronic device includes one or more parts, and a name of the part varies with a type of the electronic device.

The electronic device in accordance with various embodiments of the present disclosure includes at least one of the aforementioned components, omits some of them, or includes other additional component(s).

Some of the components can be combined into an entity, but the entity may perform the same functions as the components may do.

FIG. 14 illustrates communication protocols 900 between a plurality of electronic devices (e.g., between a wearable device, such as a smartwatch or bio signal measuring device put on the user's body) and an external electronic device 930 communicating with the wearable device 910, according to an embodiment of the present disclosure.

Referring to FIG. 14, the communication protocols 900 includes, e.g., a device discovery protocol 951, a capability exchange protocol 953, a network protocol 955, and an application protocol 957.

According to an embodiment of the present disclosure, the device discovery protocol 951 is a protocol for each electronic device (e.g., the electronic device 910 or the electronic device 930) to detect an external electronic device that the electronic device communicates with or to link itself to the detected external electronic device.

For example, the electronic device 910 (e.g., the electronic device 701) detects the electronic device 930 (e.g., the electronic device 704), as its communicable device, by its available communication scheme (such as through WiFi, BT, or USB) using the device discovery protocol 951.

The electronic device 910 obtains and stores identification information about the detected electronic device 930 using the device discovery protocol 951 in order to establish a communication link with the electronic device 930.

The 910 establishes such communication link with the electronic device 930 based on, e.g., at least the identification information.

According to an embodiment of the present disclosure, the device discovery protocol 951 is a protocol for mutual authentication between the plurality of electronic devices.

For example, the electronic device 910 performs authentication between the electronic device 910 and the electronic device 930, at least, based on communication information for linkage with the electronic device 930 (e.g., media access control (MAC) address, universally unique identifier (UUID), subsystem identification (SSID), or information provider (IP)).

According to an embodiment of the present disclosure, the capability exchange protocol 953 is a protocol for exchanging information relating to capabilities of services supportable by the electronic device 910 or the electronic device 930.

For example, the electronic device 910 and the electronic device 930 swap the information regarding the capabilities of the services that they are currently providing through the capability exchange protocol 953.

The exchangeable information includes identification information indicating particular services supportable by the electronic device 310 and the electronic device 320.

For example, the electronic device 910 can receive the identification information on the particular services provided by the electronic device 930 from the electronic device 930 through the capability exchange protocol 333.

In this case, the electronic device 910 determines, based on the received identification information, whether the electronic device 910 can be supportive of the particular services.

According to an embodiment of the present disclosure, the network protocol 955 is a protocol for controlling the flow of data that is communicated between the electronic devices (e.g., the electronic device 910 and the electronic device 930) communicably connected with each other, e.g., so that the electronic devices can provide services while interworking with each other.

For example, the electronic device 910 or the electronic device 930 can conduct error control or data quality control using the network protocol 955.

Additionally or alternatively, the network protocol 955 determines the transmission format of data communicated between the electronic device 910 and the electronic device 930.

The electronic device 910 or the electronic device 930 manages, at least, a session (e.g., session connection or session termination) for data exchange between the electronic devices 910 and 930 using the network protocol 955.

According to an embodiment of the present disclosure, the application protocol 957 is a protocol for providing a procedure or information for exchanging data related to services offered to an external electronic device.

For example, the electronic device 910 (e.g., the electronic device 701) provides a service to the electronic device 930 (e.g., the electronic device 704 or the server 706) through the application protocol 957.

According to an embodiment of the present disclosure, the communication protocols 900 is standard communication protocols, protocols designated by an individual or an organization (e.g., a communication device/system manufacturer or network provider) or combinations thereof.

The term 'module' may refer to a unit including one of hardware, software, and firmware, or a combination thereof.

The term 'module' may be interchangeably used with a unit, logic, logical block, component, or circuit.

The module may be a minimum unit or part of an integrated component.

The module may be a minimum unit or part of performing one or more functions.

The module may be implemented mechanically or electronically.

For example, the module can include at least one of Application Specific Integrated Circuit (ASIC) chips, Field Programmable Gate Arrays (FPGAs), or Programmable Logic Arrays (PLAs) that perform some operations, which have already been known or will be developed in the future.

At least a part of the device (e.g., modules or their functions) or method (e.g., operations) can be implemented as instructions stored in a computer-readable storage medium e.g., in the form of a programming module.

The instructions, when executed by one or more processor (e.g., the processor 720), enable the processor to carry out a corresponding function.

The computer-readable storage medium can be e.g., the memory 730.

At least a part of the programming module can be implemented by e.g., the processor 720.

At least a part of the programming module can include e.g., a module, program, routine, set of instructions, process, or the like for performing one or more functions.

The computer-readable storage medium includes a hardware device configured to store and perform program instructions (e.g., programming module), such as magnetic media such as hard discs, floppy discs, and magnetic tapes, optical media such as Compact Disc ROMs (CD-ROMs) and Digital Versatile Discs (DVDs), magneto-optical media such as floptical disks, ROMs, RAMs, Flash Memories, and/or the like.

Examples of the program instructions include not only machine language codes but also high-level language codes which are executable by various computing means using an interpreter.

The aforementioned hardware devices can be configured to operate as one or more software modules to carry out exemplary embodiments of the present disclosure, and vice versa.

Modules or programming modules in accordance with various embodiments of the present disclosure include at least one or more of the aforementioned components, omit some of them, or further include other additional components.

Operations performed by modules, programming modules or other components in accordance with various embodiments of the present disclosure may be carried out sequentially, simultaneously, repeatedly, or heuristically.

Furthermore, some of the operations may be performed in a different order, or omitted, or include other additional operation(s).

According to an embodiment of the present disclosure, the commands retained in the storage medium, when executed by at least one processor, may be configured to enable the processor to perform at least one operation.

The embodiments herein are provided merely for better understanding of the present disclosure, and the present disclosure should not be limited thereto or thereby.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A wearable device, comprising:
a body portion;
a strap portion coupled to the body portion, the strap portion configured to enable the body portion to be worn on a human body; and
a connection module partially disposed in a portion of the strap portion and a partially disposed in a portion of the body to couple the strap portion with the body portion, wherein the connection module comprises:
a connection pin portion provided in the strap portion to detachably couple the strap portion with the body portion; and
a holder portion mounting the connection pin portion, the holder portion provided in an end of the strap portion together with the connection pin portion,
wherein the holder portion comprises:
a holder body provided in a seating opening of the strap portion; and
a pin mounted hole passing through the holder body, wherein the connection pin portion is configured to be inserted into the pin mounted hole.

2. The wearable device of claim 1, wherein the connection pin portion comprises:
a pin body; and
a first protrusion and a second protrusion respectively extending out on two opposite ends of the pin body, wherein the first protrusion or the second protrusion is elastically driven in the pin body.

3. The wearable device of claim 2, wherein the end of the strap portion includes the seating opening adapted to receive the holder portion.

4. The wearable device of claim 1, wherein the connection pin portion comprises:
a pin body;
a first protrusion and a second protrusion respectively sticking out on two opposite ends of the pin body, wherein the first protrusion or the second protrusion is elastically driven in the pin body; and
a knob provided around an end of the pin body, the knob connecting with the first protrusion or the second protrusion to drive the first protrusion or the second protrusion.

5. The wearable device of claim 4, wherein the end of the strap portion includes a seating opening adapted to receive the holder portion, and an exposure hole is provided at a rear surface of the end of the strap portion to pass from the seating opening to a rear surface of the strap portion to externally expose the knob.

6. The wearable device of claim 5, wherein the holder portion comprises:
a holder body provided in the seating opening;
a pin mounted hole passing through the holder body, wherein the connection pin portion is configured to be inserted into the pin mounted hole; and
a guide hole positioned at the rear surface of the end of the pin mounted hole, wherein the knob is moveably seated.

7. The wearable device of claim 6, wherein the guide hole includes stopper portions protruding facing each other to stop the knob from moving.

8. The wearable device of claim 7, wherein when the holder portion is adapted to be inserted into the seating opening, the guide hole and the exposure hole are positioned to pass through each other, and when the connection pin portion is inserted into the pin mounted hole, the knob passes through the guide hole and the exposure hole to be exposed to the end of the rear surface of the strap portion.

9. The wearable device of claim 8, wherein the knob is adapted to be moved in a direction to a side in the guide hole to fit or remove one of the first protrusion and the second protrusion into or from a pin hole, at the other side, of the body portion.

10. The wearable device of claim 1, wherein the body portion includes a strap coupler portion, and wherein the strap coupler portion includes pin holes facing each other, both ends of the connection pin portion detachably fastened to the pin holes.

11. The wearable device of claim 1, wherein
the strap portion comprises a material including at least one of: urethane rubber, silicone rubber, carbon, leather, or fabric; or
the strap portion includes a carbon band obtained by processing the material with carbon.

12. A wearable device, comprising:
a body portion;
a strap portion coupled to the body portion, the strap portion configured to enable the body portion to be worn on a human body; and
a connection module provided between the body portion and the strap portion to couple the strap portion with the body portion, wherein the connection module comprises:
   a connection pin portion including a knob adjacent to an end thereof, the knob exposed to an outside of the strap portion, wherein the knob is driven to couple the strap portion to or decouple the strap portion from the body portion; and
   a holder portion provided in an end of the strap portion, the connection pin portion inserted in the holder portion.

13. The wearable device of claim 12, wherein the end of the strap portion includes a seating opening where the holder portion is seated, and an exposure hole is provided at a rear surface of the end of the strap portion to pass from the seating opening to a rear surface of the strap portion to externally expose the knob.

14. The wearable device of claim 13, wherein the holder portion comprises:
a holder body provided in the seating opening;
a pin mounted hole passing through the holder body, wherein the connection pin portion is inserted into the pin mounted hole; and
a guide hole positioned at the end of the pin mounted hole to connect to the exposure hole to externally expose the knob and moveably seating the knob.

15. The wearable device of claim 14, wherein the guide hole includes stopper portions protruding facing each other to stop the knob from moving.

16. The wearable device of claim 14, wherein the connection pin portion comprises:
a pin body inserted into the pin mounted hole and having the knob exposed through the exposure hole; and
a first protrusion and a second protrusion, respectively, sticking out on two opposite ends of the pin body, wherein at least one of the first protrusion or the second protrusion is connected with the knob and is elastically driven as the knob moves to be detachable from the body portion.

17. The wearable device of claim 12, wherein the body portion includes a strap coupler portion, and wherein the strap coupler portion includes pin holes facing each other, both ends of the connection pin portion detachably fastened to the pin holes.

18. The wearable device of claim 12, wherein the strap portion comprises a material including at least one of: urethane rubber, silicone rubber, carbon, leather, or fabric.

19. The wearable device of claim 12, wherein the strap portion includes a carbon band obtained by processing the material with carbon.

* * * * *